United States Patent [19]

Cederstrand et al.

[11] 4,320,297

[45] Mar. 16, 1982

[54] SPLIT DETECTOR

[75] Inventors: Carl N. Cederstrand, Brea; Hoke R. Chism, Jr., Anaheim, both of Calif.

[73] Assignee: Beckman Instruments, Inc., Fullerton, Calif.

[21] Appl. No.: 98,469

[22] Filed: Nov. 29, 1979

[51] Int. Cl.³ .............................................. G01J 1/00
[52] U.S. Cl. .................................... 250/343; 250/339
[58] Field of Search ............... 250/339, 343, 344, 345, 250/346

[56] References Cited

U.S. PATENT DOCUMENTS

| | | | |
|---|---|---|---|
| 2,775,160 | 12/1956 | Foskett et al. | 250/343 |
| 2,806,144 | 9/1957 | Berger et al. | 250/343 |
| 3,539,804 | 11/1970 | Billetdeaux et al. | 250/339 |
| 3,860,344 | 1/1975 | Garfunkel | 250/339 |
| 3,911,277 | 10/1975 | Cederstrand et al. | 250/344 |
| 3,920,993 | 11/1975 | Cederstrand et al. | 250/345 |
| 4,157,470 | 6/1979 | Kotaka et al. | 250/345 |

Primary Examiner—Alfred E. Smith
Assistant Examiner—Carolyn E. Fields
Attorney, Agent, or Firm—Robert J. Steinmeyer; Paul R. Harder; Edward C. Jason

[57] ABSTRACT

A gas analyzer is disclosed which provides a dual channel capability for the simultaneous determination of the presence and concentration of two gases in a stream of sample gas and which has a single infrared source, a single sample cell, two infrared bandpass filters, and two infrared detectors.

A separator between the filters and detectors prevents interchange of radiation between the filters. The separator is positioned by fitting it in a slot.

9 Claims, 6 Drawing Figures

SPLIT DETECTOR

BACKGROUND OF THE INVENTION

The present invention relates to a method and apparatus for measuring the concentration of two sample gas components in a homogeneous sample gas and more particularly to a method and apparatus for determining the concentration of sample gas constituents each having different spectral absorption bands.

Prior art has disclosed methods and apparatus for determining the concentration of several component gases in a sample gas stream. In general, the prior art requires a separate sample cell for each component gas to be measured whether two component gases are to be measured or one component and a reference is to be measured. The need for a separate sample cell for each constituent gas to be measured results in a bulky, and more expensive apparatus for routine sample measurements. The expense primarily results from the cost of an additional infrared source, a larger power supply, and a second sample cell. As a result of the need for multiple channels, manufacturing cost, both in materials and man hours, as well as maintenance costs increase proportionately. Prior art systems which do not require a separate sample cell for each sample gas component being measured required the use of time sharing electronics. Time sharing techniques necessitate the use of expensive and complex mechanics and electronics to separate the responses due to each gaseous component. One method for determining several components in a homogeneous gas sample is disclosed in copending patent application Ser. No. 13,945, "Method and Apparatus for Negating Measurement Effects of Interferent Gases in Non-Dispersive Infrared Analyzers," filed Feb. 22, 1979, abandoned, assigned to the same assignee as the present application, although the described apparatus requires several detectors and complex electronics.

SUMMARY OF THE INVENTION

The present invention comprises a single sample cell having an inlet for receiving a sample stream of gas and an outlet for exhausting the sample stream and also having an infrared source associated with it to produce incident radiant energy upon the sample stream contained within the sample cell. Opposite the infrared source is located a plurality of infrared detectors responsive to incident infrared energy. Disposed between the infrared detectors and the sample cell is a sectioned band pass filter which rejects all incident infrared energy except for selected bandwidths. Each section of the band pass filter is arranged to pass a different band of wavelengths. Thus only one infrared source and one sample gas cell are required to measure more than one component gas of a gas sample or alternately a single component gas and a reference gas.

DESCRIPTION OF THE PREFERRED EMBODIMENT

The present invention eliminates much of the cost and bulkiness of prior art multicomponent gas analyzers by a unique apparatus which can simultaneously measure multiple components of a sample gas stream while requiring only one infrared source, one sample gas cell, and a small power supply.

Figure 1:
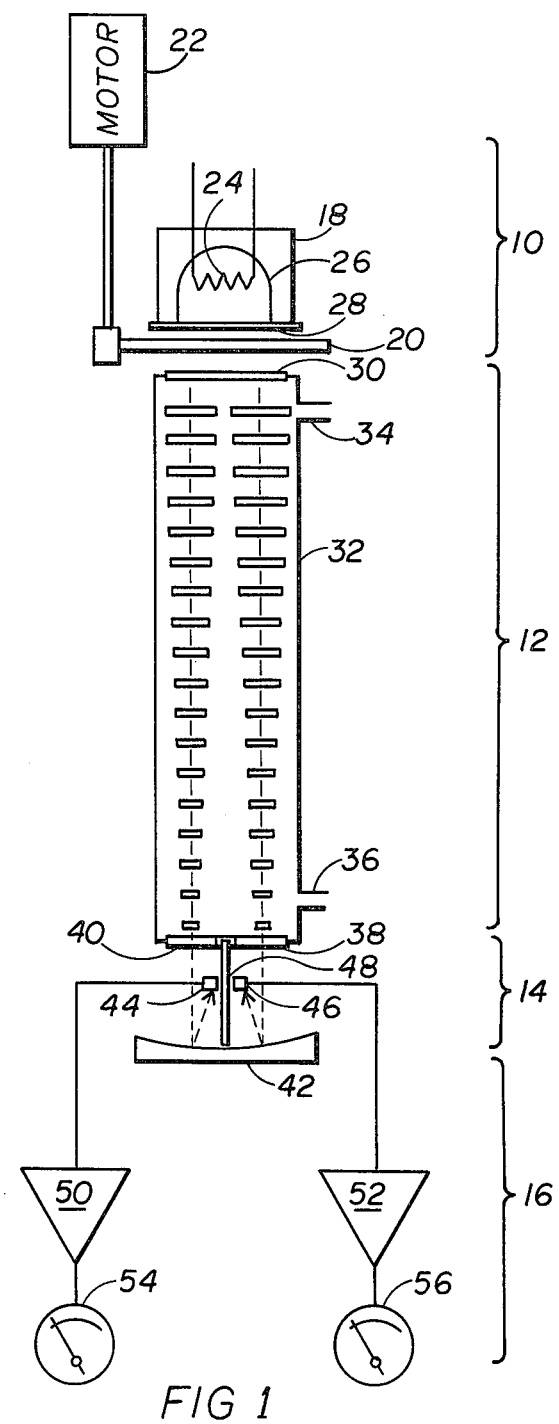
FIG. 1 is a top sectional view of the present invention.

FIG. 1 illustrates an infrared analyzer consisting of four basic assemblies. It is comprised of a source assembly 10, a sample cell assembly 12, a detector assembly 14, and an amplifier and associated electronics 16. The source assembly 10, consists of a single infrared source 18 whose radiation is periodically interrupted by a chopper blade 20 driven by an electric motor 22. The radiation from source 18 is derived from an electrically heated resistance element 24 that is located at the focus of a parabolic reflector 26. A mica window 28 fixed to the open end of the parabolic reflector 26 serves to protect the hot resistance element from air currents generated by the rotating chopper blade 20. The effect of the parabolic reflector 26 is to form substantially parallel rays of infrared radiation. These parallel rays are directed into the sample cell 12.

Sample cell assembly 12 consists of a window 30 at one end of a single sample cell 32 which transmits the interrupted infrared radiation into the sample cell. Sample gas is admitted into the sample cell through a side pipe 34 and exhausted through a side pipe 36. The other end of the sample cell 32 is sealed off by the two half filters 38 and 40 adjacent to the detector assembly 14. In the detector assembly 14, radiation passed by infrared filters 38 and 40 is focused by focusing mirror 42 on to infrared detectors 44 and 46. Radiation passed by filter 38 is focused on detector 46 while radiation passed by filter 40 is focused on detector 44. A baffle 48, which divides detector assembly 14, prevents cross talk between the two channels by blocking stray radiation from one filter from reaching the detector associated with the other filter (see FIG. 3).

Figure 4:
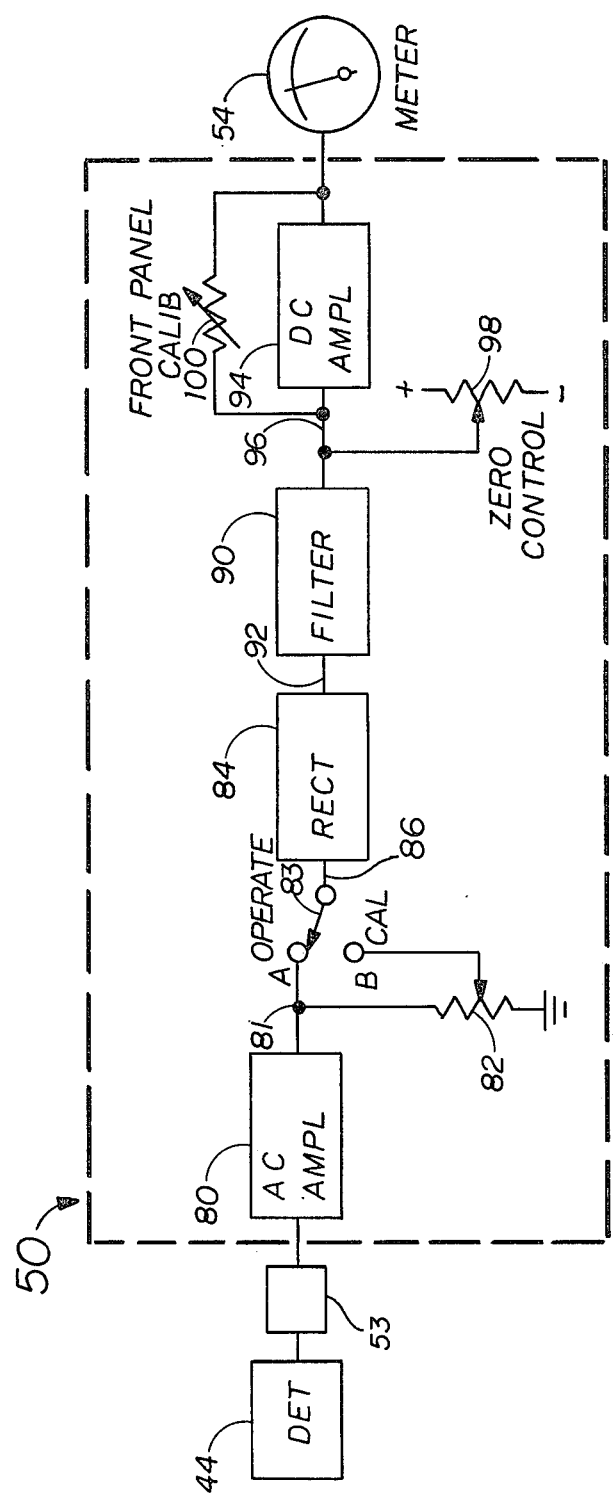
FIG. 4 is a block diagram of typical electronic circuitry of FIG. 1.

Electronics 16 is illustrated as including circuits 50 and 52. Detectors 44 and 46 will produce an electric signal proportionate to the amount of incident infrared radiation. The preferred circuitry of circuits 50 and 52 are illustrated in FIG. 4. For simplicity, since electronic circuits 50 and 52 are identical, circuit 50 is described in detail. Circuits 50 and 52 are preferably connected to detectors 44 and 46 through a suitable connector plug 53, shown in FIGS. 2 and 4. Signals from detectors 44 and 46 that are processed through circuits 50 and 52 are displayed on output devices 54 and 56 respectively. The present invention may be used in a dual beam mode wherein one of detectors 44 and 46 is used to measure infrared radiation in the band of wavelengths absorbed by the component of interest of the sample gas stream and the other detector is used to generate a reference signal. In this operation the signals from detectors 44 and 46 may be combined to produce a percent transmission signal as described in conjunction with FIG. 4.

In operation, a sample gas is admitted into the sample cell 32 through inlet 34 and exhausted through outlet 36. Sample cell 32 is filled with sample gas and subjected to pulsed incident infrared energy from the infrared energy source assembly 10. The pulsed infrared energy travels through cell 32 and is partially absorbed by some components of the sample gas stream. The component gases absorb infrared energy at characteristic wavelengths. The infrared energy, after being partially absorbed by component gases, is incident upon the bifurcated filter comprised of two separate filters 38 and 40, each passing a different band of wavelengths. The different pass bands of filters 38 and 40 are arranged to correspond to the wavelengths of strong absorption bands for two different gases, such as the primary vibrational band for carbon monoxide and the C-H stretch band for hydrocarbons or the wavelengths of the strong absorption band of one gas and an absorption band which does not correspond to any components of the sample gas stream. Thus, the concentration of a typical gas such as carbon monoxide can be determined by measuring the decrease in the amount of infrared energy that occurs at a particular wavelength bandwidth, incident upon one of the infrared detector 44 or 46 depending upon whether filters 38 or 40 are selected to pass the primary vibrational band for carbon monoxide. The amount of infrared energy absorbed by a gas in sample cell 32 indicates the amount of that specific gas such as carbon monoxide present in the sample stream. Infrared energy of a specific wavelengths passes through filter 38 and is focused by mirror 42 upon the infrared detector 46. Likewise, the amount of infrared energy passed by filter 40 is incident upon the other side of mirror 42 and is focused on detector 44. These infrared detectors, 44 and 46, may generally be any type of infared detector that will respond to the wavelengths to be measured. Thermistor flake infrared detectors are preferred in the disclosed embodiment of the present invention but it is understood that any other small infrared detectors that could be located at the focus of mirror 42 would also be suitable. As an example, either pyroelectric detectors or lead selenide detectors would be useful for measurements at lower gas concentrations, however, the signal to noise ratios of these latter two types of detectors are greater than the signal to noise ratios generally associated with thermistor flakes.

Figure 2:
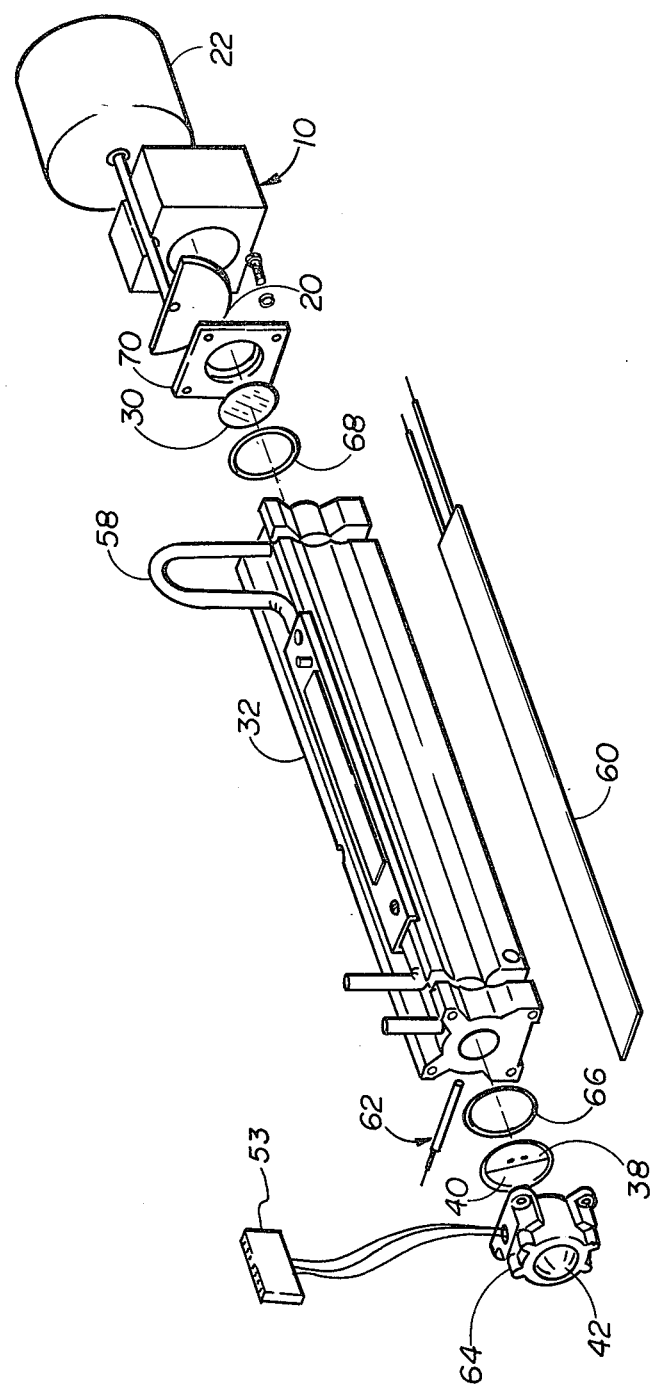
FIG. 2 is a component separated plan view of the apparatus of FIG. 1.

Referring now to FIG. 2, the actual construction of the present invention is illustrated in a component separated plan view. Infrared source 10 is illustrated in block form and may be any infrared source known in the art. Chopper blade 20 is a semicircle mounted on the shaft of electric motor 22. Blade 20 may be any material which interrupts the infrared energy being transmitted into the sample cell 32. By providing blade 20, infrared energy pulses are generated similar to those illustrated in FIG. 5. Disposed in front of infrared source 10 is sample cell window 30 which may be of any type of infrared window commonly known in the art such as sapphire or Teflon. O-ring 68 serves to seal an end cap 70 and its window 30 to the source end of the sample cell. Window 30 may be either a broad pass window or may be of a selective wavelength nature to narrow down the number of wavelengths transmitted through sample cell 32. Sample cell 32 may also be of any type known in the art. However, a metal cell having a high internal reflectivity for infrared is preferred. Sample cell 32 incorporates a preheater 58 for the incoming sample gas. The preheater 58 is a length of high thermal conductivity tubing, preferably aluminum, attached to the top of the sample cell. The sample cell 32 also incorporates an electrical base heater 60 along with temperature sensor 62 that, when connected to a temperature controller, serves to maintain the sample cell at a constant temperature. Since gases expand and contract with temperature, constant temperature operation is necessary to ensure accurate readings for any instrument that measures gas concentrations. Filters 38 and 40 are illustrated as located on the end of sample cell 32 opposite that of the infrared energy source 18. Filters 38 and 40 are illustrated as comprising a single bifurcated annular filter. Two filters are used since the optical bench shown is a dual channel bench. When additional components are to be measured, the filter may be sectioned further to provide additional channels and the necessary baffles and detecting elements may be added to the detector. Mirror 42 is located in detector housing 64 behind filters 38 and 40. O-ring 66 serves to seal the detector housing 64 and its filters 38 and 40 to the detector end of the sample cell, preventing stray air currents affecting the infrared heating of detectors 44 and 46.

Figure 3A:
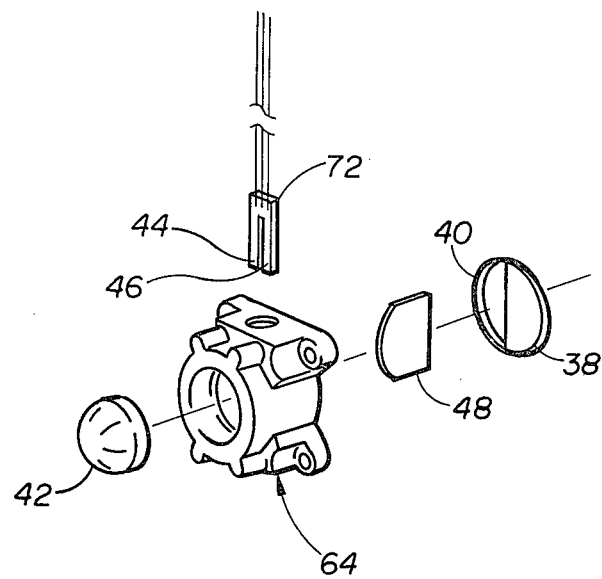
FIG. 3A is a component separated plan view of the dual channel detector shown in FIG. 2.
Figure 3B:
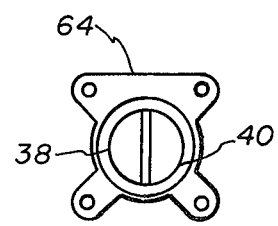
FIG. 3B is a side view showing detector housing and filters.

An exploded view of the detector is given in FIG. 3A which shows a dividing baffle 48 which fits through the slot in a substrate 72 upon which detectors 44 and 46 are mounted. FIG. 3B shows a side view of housing 64 and filters 38 and 40. Baffle 48 is disposed between filters 38 and 40 and mirror 42. Baffle 48 compartments the detector and thus prevents any interchange of radiation between filter 38 and filter 40. Located on either side of slotted substrate 72 are detectors 44 and 46 which in the preferred embodiment are thermistor flakes. The slotted substrate 72 is located in housing 64 such that it straddles baffle 48 and locates the detectors 44 and 46 at the focal point of mirror 42. However, detectors 44 and 46 may be mounted in any manner such that one is on each side of baffle 48 and will receive only incident infrared energy which is passed through one of the filters 38 or 40.

Referring now to FIG. 4, a block diagram of electronic circuit 50 with its connections to detector 44 and to meter 54 is illustrated in block form. Detector 44 feeds an a.c. signal to a.c. amplifier 80 through connector plug 53. A.c. amplifier 80 feeds an amplified alternating current signal to node 81 which feeds the signal to contact B through potentiometer 82 and contact A of calibrate switch 83. Switch 83 feeds the signal from either contact A or B to rectifier 84 through conductor 86. A rectified signal from rectifier 84 is fed to filter 90 through conductor 92. The signal from filter 90 is fed to d.c. amplifier 94 through conductor 96. D.c. amplifier 94 also receives a signal from zero control potentiometer 98 and from front panel calibration potentiometer 100 through conductor 96. D.c. amplifier 94 provides the input for meter 54 and the input to front panel calibration potentiometer 100 which is fed back to the input of d.c. amplifier 94.

In operation detector 44 produces an electrical signal which is fed to a.c. amplifier 80. This signal corresponds to the amount of infrared energy absorbed by detector 44. The signal from a.c. amplifier 80 is fed to node 81 which feeds a branch having grounded potentiometer 82 with its adjustment arm connected to contact B of calibrate switch 83 and a branch containing contact A of calibrate switch 83. Switch 83 feeds the signal from either contact A or contact B to full wave rectifier 84 where it is converted into a pulsating d.c. For means of calibration, the a.c. signal from a.c. amplifier 80 may also be reduced by a preselected amount determined by potentiometer 88 before being introduced into the full wave rectifier 84 by connecting switch 83 to contact B.

Under normal operation, switch 83 connects contact A, fed directly by the output of amplifier 80, to full wave rectifier 84. When the calibrate position, switch 83 connected to contact B is chosen, the degree of reduction in signal corresponds to that which would have been produced by the introduction of a calibration gas containing a predetermined amount of carbon monoxide into sample cell 32. In this manner, a field calibration of the instrument is attained without the use of a cylinder of calibration gas. After the signal is processed by full wave rectifier 84, the signal is fed through filter 90 which filters the signal to produce a steady d.c. signal. The d.c. signal is further amplified and processed by d.c. amplifier 94. The output of d.c. amplifier 94 is fed to meter 54 wherein it is displayed. Output device 54 is illustrated as a meter, but it is understood that a digital display would function equally well. A meter is preferred due to its reduced cost.

D.c. amplifier 94 incorporates a zero control through potentiometer 98. Potentiometer 98 allows the operator to set the output meter to zero when a zero gas is present in sample cell 32. This is achieved by providing an adjustable d.c. voltage to exactly cancel out the d.c. signal from filter 90. In this manner, output display 54 reads zero when there is no "gas of interest" in the sample cell and subsequently reads upscale when there is a "gas of interest" in the sample cell. This electronic inversion is incorporated since the signal from the detector is a maximum under zero gas conditions and then decreased as the "gas of interest" appears in the sample cell. The gain of the d.c. amplifier is adjustable and is used to set the output of the d.c. amplifier at a predetermined level when potentiometer 100 is in the calibrate position. The operator simply presses a calibrate button (not shown) and then adjusts the gain of the d.c. amplifier until output display device 54 coincides with a predetermined factor calibrate position indicated on output display 54.

The present invention may also be used in a dual beam mode wherein one detector measures an absorbing wavelength for the "gas of interest" while the other detector measures at a wavelength where no gases absorb. In this mode of operation, the electronics would, of necessity, be considerably different. In this case, the electronics associated with the two detectors would be configured to take the difference between the reference and the sample beams and then divide this result by the value of the reference beam (i.e., R-S/R where R=reference beam signal and S=sample beam signal). This would produce an output in terms of the percent transmission at the measured wavelength and hence make the instrument less sensitive to intensity variation arising from fluctuations in the source. Details of this type of circuitry are well known to those skilled in the art since this type of circuitry has been used in spectrophotometers previously. Thus, fluctuations in absorbed infrared energy due to source voltage drops, fogged filter windows, etc., are self compensating since both detectors 44 and 46 will measure the same fluctuations and the combination of the two signals will cancel simultaneous variations.

Figure 5:
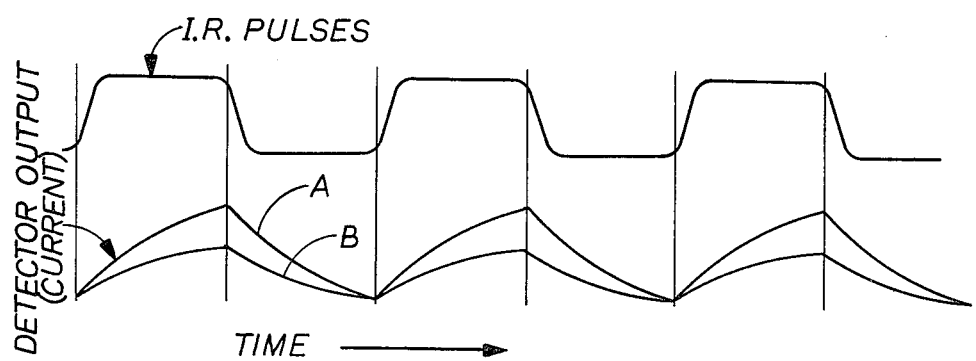
FIG. 5 is a graphical representation of the infrared pulses and the signal produced at the detector by the absorbed infrared pulses.

Referring now to FIG. 5, graphical representation A illustrates the signal produced by either detector when no absorbing gas sample is present in sample cell 32. The frequency and duration of these pulses is determined by the rotating blade. In the preferred embodiment, blade 20 (FIG. 2) is a semicircle rotating five times per second, thus generating a low frequency (5 Hz) chopping required by the detectors 44 and 46 when thermistor flakes are used. The optical bench could also be operated at a much higher chopping frequency by use of a faster, and more expensive, detector. Depending on the constituents of the sample gas stream, the pulses will be reduced in amplitude through infrared energy absorption by the component gases as illustrated by graphical representation B. Circuits 50 and 52 sense the amplitude of the signal from the detector and when adjusted properly will give an output that corresponds to the concentration of a gaseous constituent present in the sample cell.

The previously described instrument was described as operating as a dual channel optical bench with two final outputs. Each output was derived by operating the bench as two single beam benches.

The availability of these two channels also allows the bench to be configured as a dual beam single component bench. One channel would be dedicated as a sample channel and measure at a band of wavelengths where the gas of interest absorbs. The other channel would be a reference channel and hence would measure at a band of wavelengths where no gases absorb. In this manner a very inexpensive dual beam single output optical bench would be attained.

Therefore, the manufacturing cost of a multicomponent gas measuring device can be reduced by the present invention. Furthermore, the present invention reduces the size of prior art multiple gas measuring devices.

While a preferred embodiment has been disclosed, it is by way of example only and the scope of the present invention is not to be limited thereto but only limited by the proper scope of the appended claims.

What is claimed is:

1. An infrared gas analyzer comprising:
    one sample cell having a first end and a second end for receiving a sample stream of gas having several components;
    one source mounted at said first end of said sample cell for providing a source of infrared energy in said sample cell;
    detector means mounted at said second end of said sample cell and simultaneously producing a pair of output signals proportional to the amount of infrared energy incident thereon, said detector means including a substrate provided with a slot and first and second infrared responsive devices mounted on respective sides of said slot;
    first band-pass filter means mounted between said source and said detector means for passing a band of radiation at a first selected wavelength;
    second band-pass filter means mounted between said source and said detector means for passing a band of radiation at a second selected wavelength; and
    separator means located between said first filter means and said second filter means for supporting said detector means and for preventing interchange of radiation between said first and said second selected wavelengths, said separator means fitting into the slot in said substrate to position the infrared responsive devices of said detector means to receive infrared energy through respective band-pass filter means.

2. The gas analyzer according to claim 1 wherein said infrared responsive devices comprise thermistor flakes.

3. The gas analyzer according to claim 1 wherein said first selected wavelength and said second selected wavelength correspond to absorption bands of two preselected components of a sample gas stream.

4. The gas analyzer according to claim 3 wherein said first selected wavelength corresponds to an absorption band of carbon monoxide and said second selected wavelength corresponds to an absorption band for hydrocarbons.

5. The gas analyzer according to claim 1 wherein said first selected wavelength corresponds to an absorption band of a preselected component of a sample gas stream and said second selected wavelength is selected to exclude all absorption bands of all components of said sample gas stream.

6. The gas analyzer according to claim 3 or 5 wherein said first selected wavelength corresponds to an absorption band of carbon monoxide.

7. The gas analyzer according to claim 6 wherein said second selected wavelength corresponds to a region where carbon monoxide has no absorption band.

8. The gas analyzer according to claim 1 including a mirror for focusing infrared energy on said first and second infrared responsive devices.

9. The gas analyzer according to claim 8 wherein said separator means partitions the space between said first and second filter means and said mirror.

* * * * *